United States Patent

Gopinathan et al.

[11] Patent Number: 5,853,994
[45] Date of Patent: Dec. 29, 1998

[54] PARTICLE AGGLUTINATION ASSAY SYSTEM

[75] Inventors: Gopal Gopinathan, Cary, N.C.; Edmund F. Becker, Lexington, Mass.; William Wong, Milton, Mass.; Qiang Xue, Salem, Mass.; Carl M. Good, III, Groton, Mass.; John Fallon, Andover, Mass.; Xue-Song Li, Lexington, Mass.

[73] Assignee: Analogic Corporation, Peabody, Mass.

[21] Appl. No.: 761,739

[22] Filed: Dec. 5, 1996

Related U.S. Application Data

[63] Continuation-in-part of Ser. No. 350,882, Nov. 29, 1994, abandoned.

[51] Int. Cl.$^6$ ................................................. G01N 33/546
[52] U.S. Cl. ........................... 435/6; 73/61.41; 73/61.75; 73/584; 73/590; 73/599; 73/618; 73/632; 73/649; 422/20; 422/73; 422/82.01; 435/287.1; 435/287.2; 436/518; 436/523; 436/533; 436/534; 436/536; 436/806
[58] Field of Search ................................ 73/61.41, 61.75, 73/584, 590, 599, 618, 632, 649; 422/20, 73, 82.01; 435/6, 287.1, 287.2; 436/518, 523, 533, 534, 536, 806

[56] References Cited

U.S. PATENT DOCUMENTS

| | | | |
|---|---|---|---|
| 4,427,781 | 1/1984 | Masson et al. | 436/509 |
| 4,615,984 | 10/1986 | Stoker | 436/518 |
| 5,125,264 | 6/1992 | Beuzard et al. | 73/61.75 |

OTHER PUBLICATIONS

C.L. Cambiaso et al., "Particle Counting Immunoassay (PACIA). I. A General Method for the Determination of Antibodies, Antigens, and Haptens", *Journal of Immunological Methods*, 18 (1977), pp. 33–44.

C.L. Cambiaso et al., "Particle Counting Immunoassay (PACIA). II. Automated Determination of Circulating Immune Complexes by Inhibition of the Agglutinating Activity of Rheumatoid Sera", *Journal of Immunological Methods*, 23 (1978), pp. 29–50.

C.L. Cambiaso et al., "Particle Counting Immunoassay (PACIA). III. Automated Determination of Circulating Immune Complexes by Inhibition of an Agglutinating Factor of Mouse Serum", *Journal of Immunological Methods*, 28 (1979), pp. 13–23.

J.N. Limet et al., "Particle Counting Immunoassay. IV. The Use of F(ab')$_2$ Fragments and N$^{68}$ –Chloroacetyl Lysine N–Carboxy-Anhydride for Their Coupling to Polystyrene Latex Particles", *Journal of Immunological Methods*, 28 (1979), pp. 25–32.

E. Henkel, "Marker Free Immunological Analytical Methods", *J. Clin. Chem. Clin. Biochem.*, vol. 22, 1984, pp. 919–926.

*Primary Examiner*—Christopher L. Chin
*Attorney, Agent, or Firm*—Lappin & Kusmer LLP

[57] ABSTRACT

A system for assaying a fluid sample for one or more types of analytes, which employs at least one class of finely divided polystyrene spheroidal particles, each class being limited to a predetermined specific narrow range of particle diameters, the particles of each such class being coated with a specific reactant unique for that class. After the coated particles are mixed with the sample to specifically react to form conjugates of the particles and any of the analyte present, the mixture is irradiated with bursts of ultrasound swept over a range of frequencies resonant to the expected conjugate sizes. The presence of the conjugates and therefore the analyte is detected directly by measuring any selective absorption or scattering of waves of frequencies to which the conjugates are resonant.

36 Claims, 5 Drawing Sheets

PARTICLE AGGLUTINATION ASSAY SYSTEM

This application is a continuation-in-part of U.S. application Ser. No. 8/350,882 filed Nov. 29, 1994, now abandoned.

This invention relates to chemical and biochemical assay systems, and more particularly to improved particle agglutination assay systems.

BACKGROUND OF THE INVENTION

Assays are well known in which aliquots of a liquid test sample containing one or more analytes are variously reacted with one or more reagents in highly specific reactions to form analyte complexes such as antigen/antibody or similar complexes which may then be observed in order to assay the sample for the presence of a predetermined moiety or analyte in the sample. Typically, an antibody is used to assay for the presence of an antigen against which the antibody was specifically induced and reactable, but such assays have been extended to other specific reactions to quantitate analytes including haptens and other molecules such as hormones, alkaloids, steroids, antigens, antibodies, nucleic acids, enzymes and fragments thereof. It is in this broad sense that the term "analyte" as used herein should be understood to refer to that which is being sought in an assay and is deemed to include antigens, haptens, antibodies and other molecules, the presence and/or quantity of which is being assayed. It will therefore be appreciated that the assay of the present invention has broader applications than immunoassays per se. The phrase "specific reaction" and variants thereof are to be understood to refer to a reaction, such as an antigen/antibody reaction and the like that are understood to exhibit very high specificity.

A substantial body of prior art exists relating to a specific form of immunoassay known as particle agglutination assay, sometimes referred to as PACIA systems. Much important work on PACIA systems originated by a group in Belgium and is published in, for example, Particle Counting Immunoassay (PACIA). I. A General Method for the Determination of Antibodies, Antigens and Haptens, C. L. Cambiaso et al, *J. Immuno. Meth.*, 18 (1977) 33–34; Particle Counting Immunoassay (PACIA). II. Automated Determination of Circulating Immune Complexes by Inhibition of the Agglutinating, Activity of Rheumatoid Sera, C. L. Cambiaso et al, *J. Immuno. Meth.*, 23 (1978) 29–50; Particle Counting Immunoassay (PACIA). III. Automated Determination of Circulating Immune Complexes by Inhibition of an Agglutinating Activity of Mouse Serum, C. L. Cambiaso et al, *J. Immuno. Meth.*, 28 (1979) 13–23; and Particle Counting Immunoassay. IV. The Use of F(ab')$_2$ Fragments and $N^{68}$-Chloroacetyl Lysine N-Carboxy-Anhydride for Their Coupling to Polystyrene Latex Particles, N. Limet et al, *J. Immuno. Meth.*, 28 (1979) 25–32. These articles and later papers based on this work, including U.S. Pat. No. 4,427,781, teach mixing the sample with an agglutinating agent and reactant-coated latex particles, and counting the unagglutinated or free particles with a light-scattering optical device of the type intended to count blood cells in an autoanalyzer format, e.g. the Technicon PACIA System (Technicon International Division, Geneva, Switzerland). The authors claim that this is a particularly suitable technique to obtain practical and sensitive measurements of various analytes. It should be noted that because this method measures agglutination indirectly by counting the unagglutinated particles, it requires a prior knowledge of the initial amount of particles used in the assay. Thus, unless the total number of particles employed is known ab initio, that method cannot serve for qualitative detection. Further, that method is limited to measurement of one analyte at a time, so lacks speed and flexibility.

Nephelometry and turbidimetry, two alternative optical methods used to measure particle agglomeration, are discussed in Marker-Free Immunological Analytical Methods, E. Henkel, *J. Clin. Chem. Clin. Biochem.*, 22 (1984) 919–926 which points out the many disadvantages of these two methods.

A principal object of the present invention is therefore to provide an improved assay system of the type described, in which the problems of the prior art are overcome by providing a simple, low-cost system which provides direct information regarding the presence and/or quantity of agglutinated particles. Other objects of the present invention are to provide such a system in which the presence of one or more analytes is detectable qualitatively in the same sample, to provide such a system in which the presence of more than one analyte being assayed can be detected substantially simultaneously, and to provide such a system in which agglutinates or conjugates formed of two or more particles (hereinafter respectively "diglutinates", "triglutinates", etc.) from the same class of particles are readily detected by absorption or scattering of pressure waves at observed frequencies.

Yet another object of the present invention is to provide an electroacoustic system for quantitatively and qualitatively assaying the presence of analytes in a sample solution based on measurement of the change of the forward energy of acoustic waves caused by the conjugates.

Other objects of the present invention will in part be obvious and will in part appear hereinafter.

SUMMARY OF THE INVENTION

To effect the foregoing and other objects, the present invention generally is a system for assaying a fluid sample for at least one analyte, which system employs a reagent comprising at least one class of minute, substantially spheroidal initial particles, the particles of such class being limited to within a predeterminedly narrow range of particle diameters. The particle of such class are typically pre-coated with a reactant capable of entering into a reaction involving the analyte to thereby generate resultant particles having dimensions different than the dimensions of the initial particles. When the reaction is a highly specific binding reaction and the analyte has more than one attachment site for that binding reaction, the resultant particles will be conjugates (i.e. clumps or links of particles) formed initially typically as diglutinates or triglutinates of the coated initial particles. The presence of those conjugates is detected by irradiating those conjugates with compression or sound waves in a frequency range at which the conjugates will cause a reduction or attenuation, as by scattering, absorption and the like, in the forward energy of the sound waves within a wavelength band determined in accordance with the scattering cross-section of the conjugates. Where the reactant bonded as a coat on the particles is the same as the analyte sought to be assayed, another reagent, specifically reactable with that analyte, is introduced to provide linkage between the immobile, bound reactant on the particles and the mobile or free analyte in the sample. Sensor means are provided for detecting and/or measuring the reduction of the forward energy by the conjugates. It is preferred that the compression waves provided are ultrasonic, and desirably, the ultrasonic energy generator may also serve as the sensor.

In yet another embodiment of the present invention, the initial particles in the reagent are linked conjugates of minute, substantially spheroidal particles, and the linkage between the particles is characterized as being cleavable by the reaction involving the analyte so as to release individual spheroidal particles as the resultant particles.

Another particular embodiment of the present invention permits one to assay simultaneously for plural analytes in a given sample. To this end, this embodiment employs a like plurality of classes of minute, substantially spheroidal particles, each such class being characterized by a correspondingly unique, narrow range of particle diameters. In such case, the particles of each such class are precoated with a respective reactant capable of entering into a highly specific reaction involving corresponding ones of the several analytes in the sample., thereby providing conjugates, each formed entirely out of particles of the same size from a given class. Each such conjugate then has an acoustic scattering cross-section unique to each combination of plural particles of a given diameter from a given class and the corresponding analyte.

Yet another embodiment of the present invention is based on the finding that agglutinates formed by binding of small particles (e.g. 1 $\mu$m in average diameter) to larger particles (e.g. 5 $\mu$m in average diameter), produces a more pronounced and improved effect on scattering over a specific frequency range of an acoustic signal than do agglutinates formed by binding large particles to one another. Accordingly, another object of the present invention is to provide an assay system of the type described which employs at least two classes of minute, substantially spheroidal particles coated with a reactant capable of entering into a binding reaction with high specificity. Each such class is limited to particles lying within a predeterminedly narrow range of particle diameters, the average diameter of the particles in one of the classes being at least twice as large as the average diameter of the particles in the other class. Where the smaller particles are present in much larger number in the mixture, the conjugates will statistically form predominately initially as a large particle to which a number of smaller particles have adhered. The particle size within the class of smaller particles is selected such that they exhibit acoustic scattering substantially outside of the bandwidth of the sensor means. In such case, the sensor is selected to have a bandwidth that normally will detect acoustic scattering by both the larger particles of the first class and conjugates of the preferred magnitude initially formed by reaction among the particles of the two classes, but neither the smaller particles of the other class nor the very large conjugates formed later will exhibit acoustic scattering substantially within the bandwidth of the sensor.

The invention accordingly comprises the apparatus possessing the construction, combination of elements and arrangement of parts, and the method comprising the several steps and the relation of one or more of such steps with respect to each of the others, all as exemplified in the following detailed disclosure, and the scope of the application of which will be indicated in the claims.

BRIEF DESCRIPTION OF THE DRAWINGS

For a fuller understanding of the nature and objects of the present invention, reference should be had to the following detailed description taken in connection with the accompanying drawing wherein.

DETAILED DESCRIPTION OF THE DRAWINGS

Figure 1:
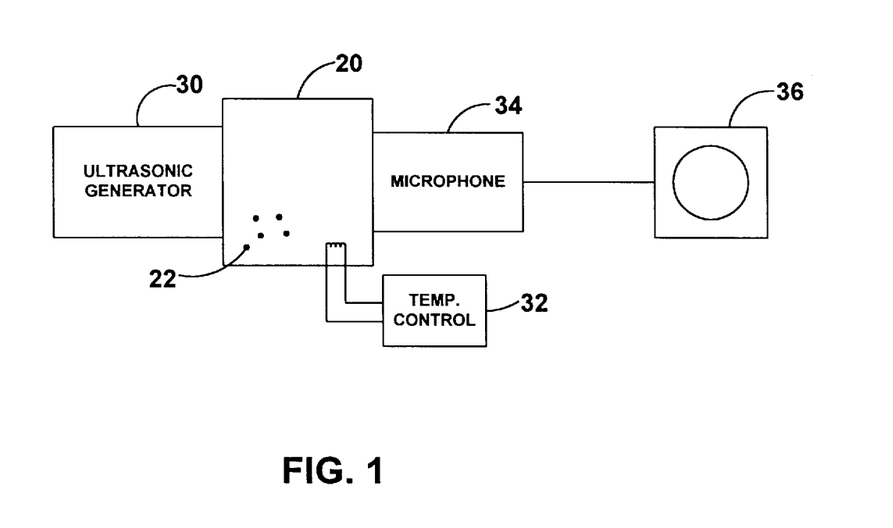
FIG. 1 is an idealized diagrammatic representation, partly in cross-section, of an assay system embodying the principles of the present invention.

In FIG. 1 there is shown one exemplary system for assaying fluid sample 20, and which preferably employs at least one of a plurality of classes of different narrow ranges of diameters of minute, spherical or spheroidal particles 22 substantially chemically inert to sample solution 20 and to the reagents to be used in the assay method. The diameters of particles 22 of the several classes may broadly be within the range from about 0.1 $\mu$m to about 50 $\mu$m, but preferably lie within a more restricted total range of from about 0.5 $\mu$m to about 10 $\mu$m in average diameter. Each class of particles is, however, characterized as being limited to a definitive, predetermined small range of particle diameters, e.g. the particles of each class being within a range of diameters typically 0.2 $\mu$m wide, e.g. the particles in a class of nominally 2 $\mu$m diameter are distributed within a range of diameters of 2±0.1 $\mu$m. The particles in each such class are coated with a sheath or coat 26 of at least one reactant, such as an antibody, immobilized on the particle, and which reactant is preferably unique to that class of particles. The particles of each such class may also be coated with a plurality of types of reactant which may also be unique to that class of particles, each of that plurality of types of reactant being couplable with a corresponding, distinct analyte to form corresponding conjugates. The reactants can be not only antibodies, but low molecular weight haptens, antigens, enzymes, and other biological and chemical receptors that characteristically enter into highly specific reactions with other ligands. Particles 22 are typically of white polystyrene latex beads (commercially available from Interfacial Dynamics Corp., Seattle, Wash.), but can readily be made of other polymers, glass and the like.

Figure 2:
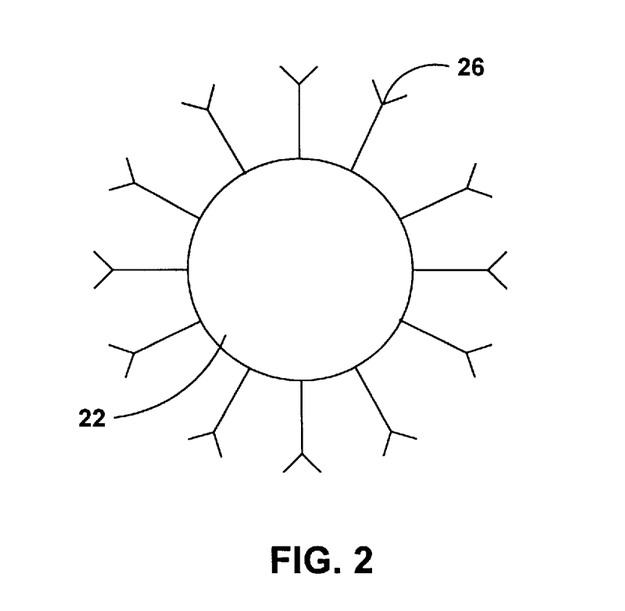
FIG. 2 is an enlarged schematic representation of a coated particle used in the present invention.
Figure 3:
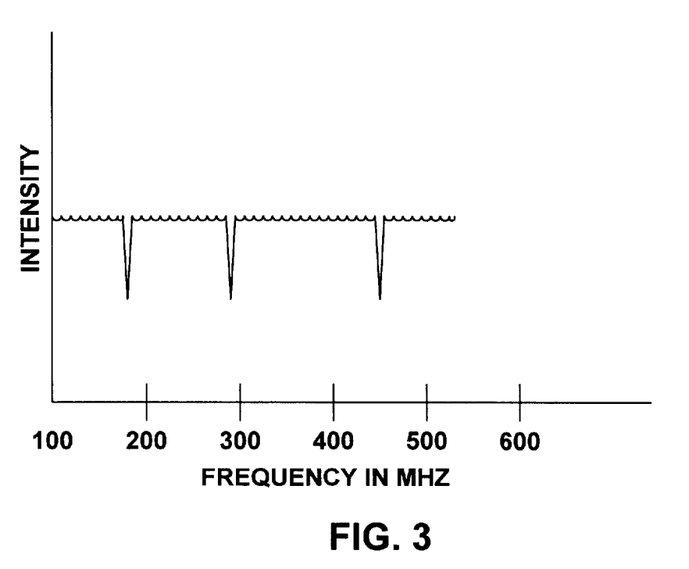
FIG. 3 is a graphical representation in which frequency is plotted against sound intensity to indicate scattering dips corresponding to agglutinate sizes.

In one particular example, two classes of white polystyrene latex beads 22, one class having average diameters of 2.0±0.1 $\mu$m, the other having average diameters of 5±0.1 $\mu$m, are each provided with a respective unique coat 26 and 28 as shown in FIG. 2. For example, the particles of one class are coated with a polypeptide antigen derived from HIV-1 env genes, and the particles of the other class are coated with another polypeptide antigen derived from HIV-2 env genes. Because proteinaceous materials are readily adsorbed onto the surface of hydrophobic polystyrene, simple immersion in a suspension or solution containing the proteins will result in the latter being fixedly bonded to the particles as a coating. Of course, other techniques, such as covalent bonding, for coating such particles with antibodies, antigens and the like, have been extensively documented in the prior art and need not be further described here.

Such exemplary coated particles are then used to assay a body fluid such as blood, for HIV-1 and HIV-2 by mixing the two groups of coated particles into sample 20 of body fluid. This exemplary assay is particularly use where antigens such as HIV tend to be present in tissues such as liver and the like, but usually only at extremely low concentrations in blood serum, if at all, whereas the antibody is much more likely to be available in the serum. Antigen coatings 26 on particles 22 will specifically react with the precise viral antibodies, if present, in sample 21. Because typically an antibody has more than one reactive site, it will initially tend to couple to one or more particles coated with the specific antigen or hapten to that antibody, specifically reacting to form agglutinates or conjugates. This agglutination process is rate-sensitive in that the agglutinates formed initially are diglutinates, triglutinates and the like, although ultimately larger and larger conjugates will tend to grow or be created.

Thus, the class of smaller diameter particles described above would tend to form agglutinates or conjugates initially having approximate scattering cross-sections of about 4 $\mu$m and about 6 $\mu$m, and the class of larger diameter particles then would tend to combine with others of its own class to form conjugates initially having approximate scattering cross-sections of about 10 $\mu$m and about 15 $\mu$m. These different scattering cross-section will effect an diminution or attenuation in the forward energy of the irradiating waves within wavelength bands that can be correlated with the scattering-cross sections and thereby identify the analyte contributing to the formation of the particular conjugate.

Figure 5:
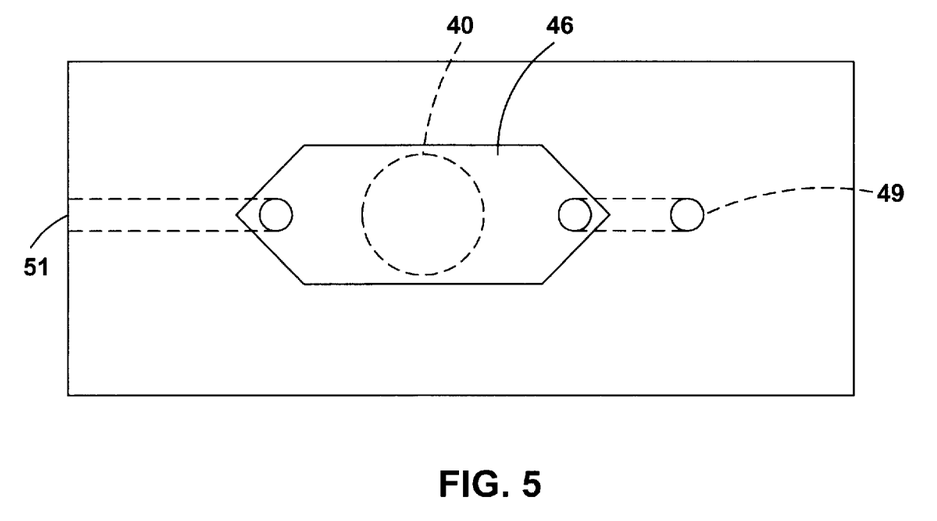
FIG. 5 is a plan view of a flow cell particularly useful in carrying out the process of the present invention.
Figure 6:
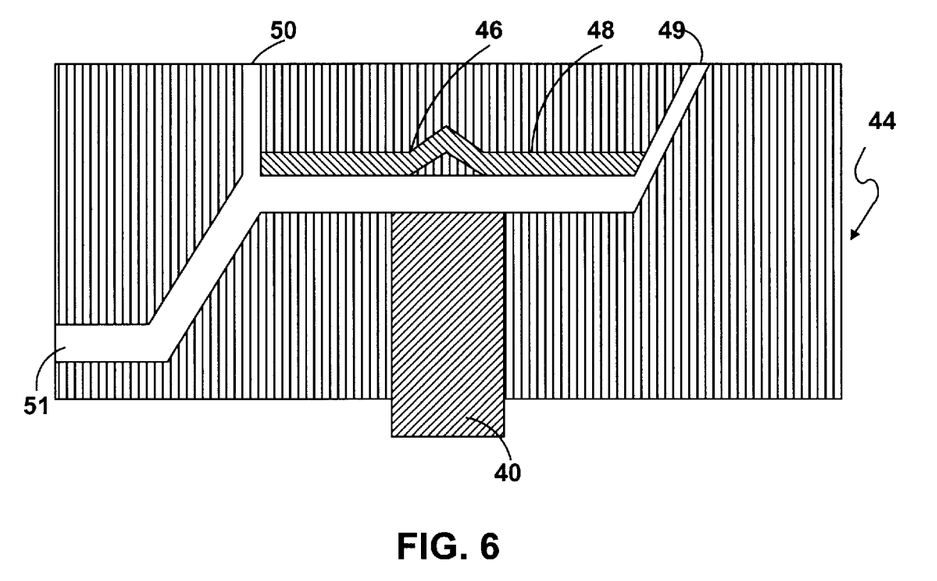
FIG. 6 is elevational cross-section through the flow cell of FIG. 5.

The present invention can readily use as many as four different classes of coated particles, in which case one must select the range of sizes of the particles carefully to avoid the possible creation of diglutinates and triglutinates that might have the same or closely matched scattering cross-sections as other conjugates or classes of particles.

Agglutination can be demonstrated by the following example which is presented merely as exemplary of a specific embodiment and is not intended to provide any limitation to the invention as claimed hereinafter. For an assay for human thyroid stimulating hormone (hereinafter TSH), polystyrene spheres of average 1.62 $\mu$m diameter are coated with anti-TSH monoclonal antibodies by incubating the spheres overnight in a solution of 100 mg/ml of antibody in 10 mM HEPES buffer, pH 7.5. The coated spheres are recovered by brief centrifugation, and washed three times in a 4-fold volume of 10 mM HEPES buffer, pH 7.5, containing 0.1% (w/v) BSA and 0.01% $NaN_3$. The recovered, coated spheres are then suspended in 20 mM glycine buffer, pH 9.3, containing 0.1% (w/v) BSA, 0.01% $NaN_3$, and 300 mM NaI to form a reagent. The initial concentration of single spheres in this reagent are about $5\times10^7$ spheres/mL. Diglutinates, present in the unreacted reagent as the result of the manufacturing and coating processes, are typically about 2% of the initial single sphere concentration. This reagent is then added to an equal volume of standard human serum (OEM Concepts, Inc., Toms River, N.J.) containing known concentrations of human TSH, and stirred continuously to effect a reaction between the coated spheres and the human TSH. Mixing can also be achieved without stirring. Sampling of reaction mixtures by the apparatus of the present invention during the first several seconds following initiation of the specific reaction between the particles and the analyte, detected the presence of diglutinates and triglutinates well in excess of those created by the manufacturing and coating processes.

Means, such as source 30 of compression waves, are provided for bulk insonifying the reacted mixture of body fluid 20 and particles 22 with a flux of compressional waves such as ultrasound, typically swept through a frequency range over which detectable attenuation effected by the scattering for particles of the size involved can be expected. It is apparent that the range of frequencies employed depends on the propagation velocity of the compressional waves through the bulk of the sample medium, which itself depends on such factors as temperature, pressure and density.

Thus, one can consider an assay employing two different classes of particle to assay for two different analytes. Using exemplary values of scattering cross-sections of about 4 $\mu$m and about 6 $\mu$m for the expected two and three-particle conjugates in the first class of particles, and about 10 $\mu$m and about 15 $\mu$m for similar groups or conjugates of the second class of particles, for a liquid sample at normal pressure and 25° C. with a density close to sea water so that the nominal velocity of a compressional wave in that medium would be about 1530 m/sec., the frequencies corresponding to scattering minima for these conjugates would lie in the range of between about 100 MHz to 500 MHz. It will be recognized that the agglutinated particles are typically asymmetrical, so the detected attenuation of scattering frequency bands will not necessarily be sharply defined. Because the system can be quite temperature sensitive, it is preferred to provide known temperature controlling apparatus shown schematically at 32, to maintain the temperature of the sample solution during assay at a fixed, predetermined level. Preferably, ultrasound is applied from source 30 in bursts, each of which is swept through the desired frequency range, to permit one to broadcast and then listen, so that each agglutinated complex can cause scattering that attenuates the forward energy of the ultrasound at one or more characteristic frequency bands or otherwise change the characteristics of the compression waves within the swept range of the input waveburst. Measurements are preferably taken only during the first several seconds following initiation of the specific reaction between the particles and the analyte in order to detect the presence of diglutinates and triglutinates before formation of much larger agglutinate masses that may interfere with the assay.

As shown in FIG. 1, generator 30 and detecting microphone 34 may be provided as separate devices, but alternatively as shown in FIG. 4, sonic reflector 38 can be positioned in place of microphone 34, and the same transducer 40 can serve, as well known in the art, alternately as both a sonic generator and receiver. It should be noted that the embodiment of FIG. 4 particularly includes sonic delay line 42 to introduce a delay into the propagation of the sonic bursts sufficient to permit detecting circuitry to switch between transmission and reception of the energy of the compression waves.

In a preferred detail of the embodiment of FIG. 4, as shown in FIGS. 5 and 6, the flat output face of acoustic transducer 40 is mounted adjacent one side of hollow flow cell 44 that includes capillary flow channel 46 directed normally to the direction of acoustic propagation from transducer 40. Acoustic reflector 48 is positioned on the other side of the cell 44 so that channel 46 is positioned between transducer 40 and reflector 48. For clarity in illustration, the delay line of FIG. 4 is not shown in FIGS.

5 and 6. The dimension of channel 46 are such that normal saline and other liquid samples will wick into the flow cell without any driving force other than capillary action, so typically the height of channel 46 is several thousandths of an inch. The use of capillary dimensions for channel 46 minimizes the number of mechanical components and control circuits required by the flow cell, and importantly provides for very gentle entry of fluid into the cell so as to minimally dissociate agglutinated particles.

To fill cell 44, air in the flow cell must be permitted to escape as liquid enters into inlet conduit 49, and to this end, cell 44 is provided adjacent the outlet end of channel 46 with a narrow, vertical air vent 50. Evacuation of channel 46 is preferably effected by a vacuum applied at outlet conduit 51 connected to channel 46. Although vent 50 will be open, because its internal diameter is preferably much smaller than the diameter of channel 46, air flow through vent 50 will be restricted, causing most of the vacuum pressure to be applied to channel 46, thereby evacuating the latter.

Figure 7:
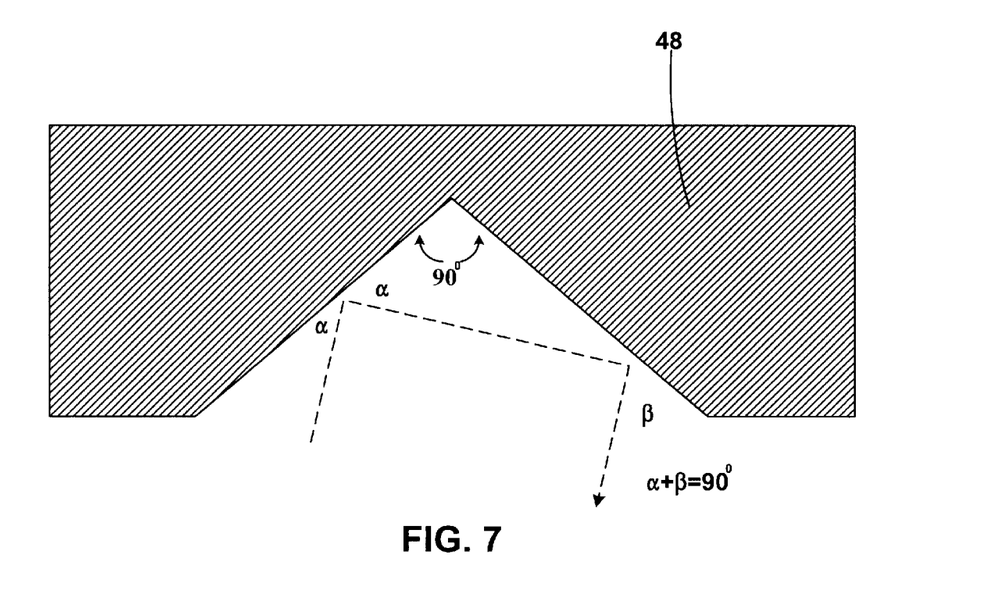
FIG. 7 is elevational cross-section diagram of a self-aligning reflector useful in the embodiment of FIG. 5.

Experiments have shown that sonic reflector 48 must be aligned parallel to the plane of transducer 40 at within about 1 angular degree to prevent excessive signal loss. Accordingly, as shown in FIG. 7, a preferred form of reflector 48 is configured as a hollow 90° cone which provides the property of returning the reflected wave in a direction parallel to the incident wave inasmuch as the angle between incoming and outgoing waves (shown in broken line) is $2\alpha+2\beta$ which, because $\theta$ is 90° by definition, must be equal to 180°.

Figure 4:
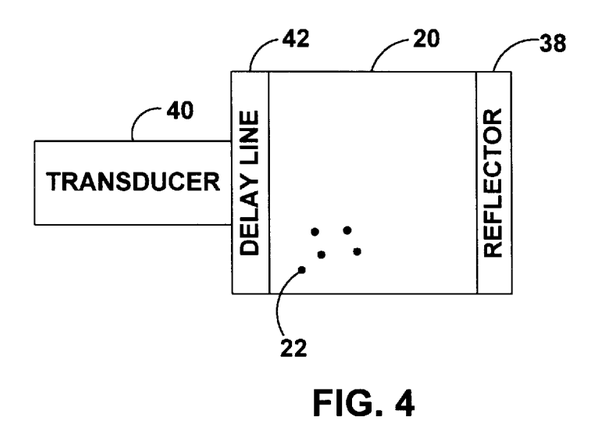
FIG. 4 is an idealized, diagrammatic, cross-sectional representation, of another embodiment of an assay system incorporating the principles of the present invention.

Exploiting the concepts of the ultrasonic immunoassay of the present invention in a clinical instrument requires methods of not only delivering and receiving the ultrasonic energy to and from the sample, but processing and interpreting the received signals. Because particles in the sample of the appropriate size relative to the wavelength of the incident sound wave will cause some portion of the energy to be absorbed and some portion to be reflected back to the transmitter in the embodiment of FIG. 4, the received signal preferably being gated in time to selectively accept certain parts of the reflected signal.

Thus, both time and amplitude changes in the received energy can be related to signal scattered energy.

If the transmitting transducer is excited with a short pulse, the resulting transmitted sonic wave has a wide spectrum with energy in all of the frequencies in the band. The shape of the spectrum is directly related to the shape of the excitation pulse. The received spectrum will be altered by the characteristics of the elements in the path, including the sample. Signal attenuation due to an agglutination reaction as a function of acoustic frequency can be measured quantitatively by measuring the spectra with and without reactants and comparing the two.

The transducer can be excited with a continuous signal of a single frequency. The frequency can be varied to sample particles of different sizes. The signal can be continuously varied (swept) in a sawtooth or triangular format to produce a spectrum as a function of time. The transducer can be excited with a continuous signal composed of a superposition of individual signals of single frequencies, each corresponding to a wavelength of interest. The received signal can be decoded using bandpass filters and the relative amplitudes compared to provide a measure of attenuation at each frequency.

In all cases above, a single frequency which is unaffected by any of the particles used or combinations of particles used can be established as a reference providing a measure of energy in the transmitting signal and which can be used to normalize all other received signals. The measurements can be made continuously as the reaction progresses from no agglutination to completion. Agglutination reaction rates are typically related to temperature, so the measured signal will be also be related to the temperature of the reaction and the time from inception at which the measurement is made. By making continuous measurements from the inception of a reaction, the reaction rate can be calculated, thus obviating maintenance of constant temperature or monitoring of temperature. If the measured signal, S, (regardless of what system is used to measure the attenuation due to scattering for a given particle size) is a function of time as follows:

$$S = A(1 - e^{(-t/\tau)}) \quad (1)$$

where

A is the measure of the agglutinated particles to be determined and $\tau$ is the time constant of the reaction and is related to temperature.

The time derivative of the measured signal $S_t$ is $$dS/dt = (A/\tau)e^{(-t/\tau)} \quad (2)$$

The measured signal, S, and the derivative of the measured signal, dS/dt, which can be calculated, assuming sufficient samples of S are available, can be used to calculate $\tau$ as follows, $$S = \tau[dS/dt_{(t=0)} - dS/dt] \quad (3)$$

Once $\tau$ is known, A can be calculated irrespective of the temperature of the reaction.

Figure 8:
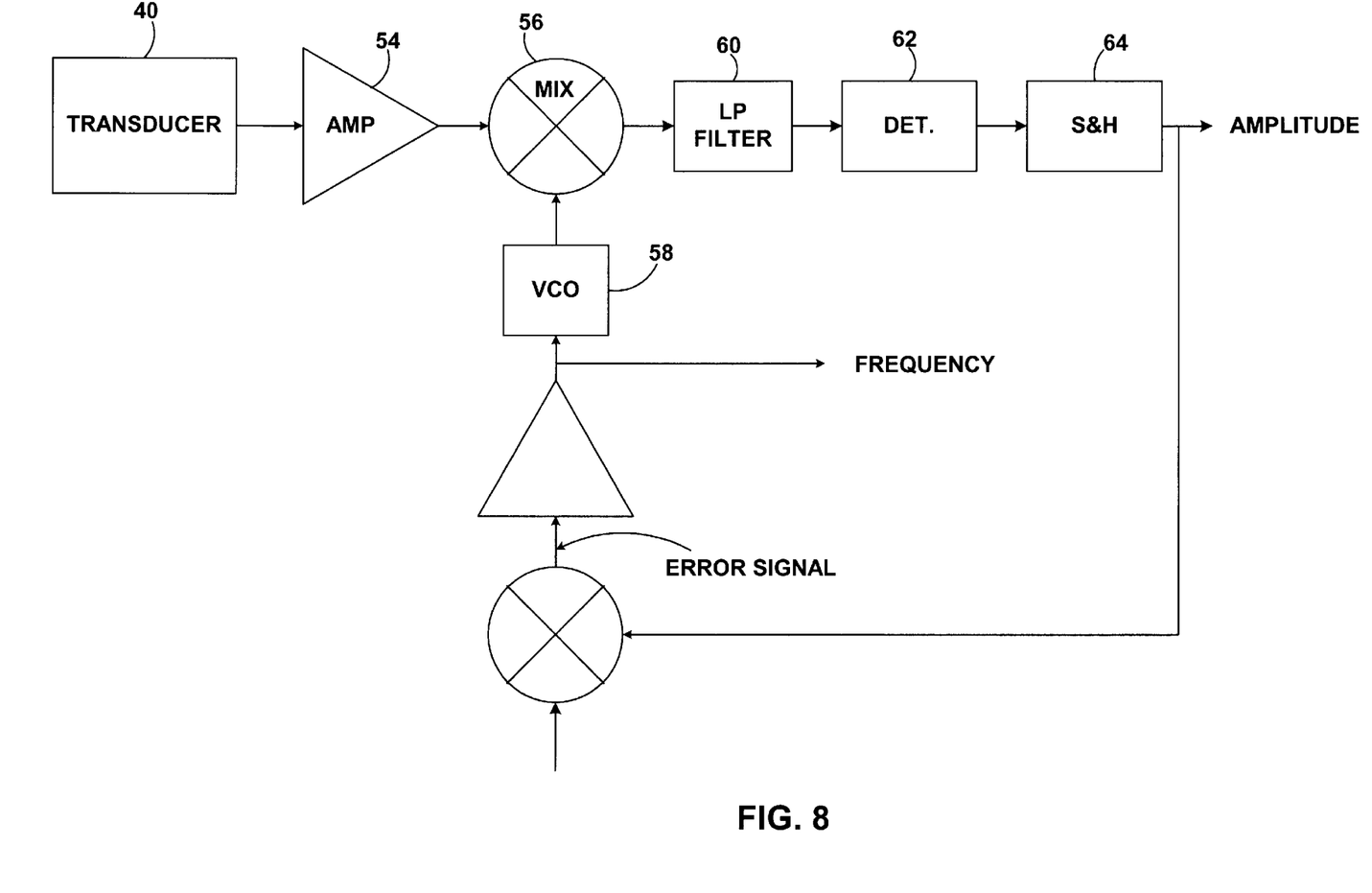
FIG. 8 is a block diagram of a partial schematic circuit for determining the frequency and amplitude of signal changes due to scattering in the spectrum of the received signal of an embodiment of the apparatus of the present invention.

FIG. 8 shows typical apparatus for determining the frequency and amplitude of a dip due to scattering in the spectrum of the received signal. The transmitting part of the apparatus is not shown. The transmitted signal can be a short pulse, producing a wideband spectrum, but is not limited to that implementation inasmuch as continuous excitation can also be used. The signal received by transducer 40 is amplified in amplifier 54 and then multiplied in RF mixer 56 with a sinusoidal signal from voltage controlled oscillator 58. The low frequency product of mixer 56 is passed by bandpass filter 60 which rejects other signal components. The energy of the resulting signal from filter 60 is detected by detector 62 and held in sample-and-hold circuit 64 until the next sample is received. The detected signal in sample-and-hold circuit 64 is continuously compared with signal common to produce an error signal which controls the frequency of the oscillator 58. The circuit of FIG. 8 will lock onto a dip in the received spectrum and track it as the reaction progresses. The input voltage to oscillator 58 provides a measure of the frequency of the dip and the output of sample-and-hold circuit 62 represents the amplitude of the dip. Other circuitry, not shown explicitly, is required to maintain stability of the feedback loop and to cause the frequency of oscillator 58 to stay within a prescribed range when no dip is present.

Simultaneous processing of multiple analytes is complicated by overlap of the attenuation spectra associated with each particle size to be measured. The situation is compounded because the attenuation spectrum for a given diameter is not monotonic; several dips occur at different frequencies. The following method of signal processing permits overlapping spectra to be separated.

Attenuation of ultrasound waves by small particles can be modeled in terms of scattering or absorption cross section.

At a particular wavelength (or equivalently, frequency), particles of diameter, $D_1$, have an effective cross section area, $s_i$. In a given sample, the total attenuation, K, at a given wavelength or frequency for all particles, $D_1$, is $$K = s_i N_i \quad (4)$$

where $N_i$ is the number of particles, and the received signal is $$E_o = E_{in} s_i N_i \quad (5)$$

In a population of m different diameters, $$E_o = E_{in} \sum_{i=1}^{m} s_i N_i \quad (6)$$

Note that for a given particle diameter, $s_i$ varies with wavelength.

Figure 9:
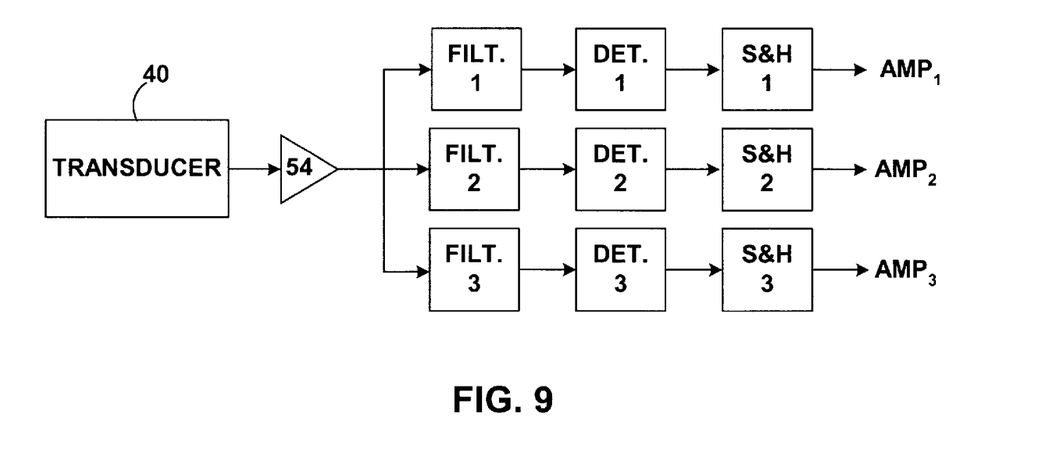
FIG. 9 is another block diagram of an alternative partial schematic circuit for determining the frequency and amplitude of signal changes due to scattering in the spectrum of the received signal of an embodiment.

Consider the variation of the embodiment of FIG. 8 shown in FIG. 9 in which an ultrasound transducer 40 is followed (omitting the mixer-VCO loop for simplicity) by a number of different bandpass filters in parallel, each followed by a corresponding energy detector and a respective sample-and-hold circuit. The output of each filter path, expressed as a matrix, is $$[E_j] = E_{in} [s_{ij}][N_i] \quad (7)$$

If j is greater or equal to i, and if $E_{in}$ and so are known, then one can solve for $N_i$. The filters in such case should be designed so that $s_{ij}$ is maximized on the diagonal and minimized elsewhere, particle diameters being selected to promote this design.

It will be understood that with four different classes of particles, each class having a unique size of diglutinates and triglutinates, there can be at least twelve different scattering frequency bands at which attenuation occurs, which when spread across the swept frequency spectrum provide separations of about 25 MHz between absorption valley centers. Attempts to obtain scattering data regarding agglutinates larger then four particles tend to become extremely complex, so the present assay by the embodiment thus described is preferably limited to measurement of the smaller agglutinates formed during the earlier or initial phases of the agglutination reaction. The extent of attenuation, typically through scattering, by agglutinates of particles 22 depends, inter alia, on the difference between the density of particles 22 and the density of the surrounding medium. For example where the densities of the particles and the medium are close, scattering by the particles will be heavily damped and sharp valleys in the scattering spectrum will usually not be observed. It is believed that for this reason, there has been negligible difficulty in detecting attenuation of conjugates of polystyrene spheres in whole blood, notwithstanding that the blood corpuscles may be of the same approximate size as the conjugates. Hence it is preferred to employ particles having at least 10% difference in density than the surrounding or supporting fluid medium. As earlier noted herein, the attenuation bands caused by the scattering from agglutinates of particles 22 can be readily detected by the sonic transducer per se or a separate microphone, the output of both of which is preferably connected to appropriate signal processing devices or apparatus 36 as shown particularly in FIG. 8, which may include a chart recorder or the like.

Thus, for example, if the input ultrasound has a flat spectrum over the entire 100 to 500 MHz range, then there will be absorption valleys in the output, as shown in FIG. 3, displayed on chart recorder of apparatus 36 and taken within about 1 to 5 minutes following initiation of the agglutination reaction. Each such valley shown in FIG. 3 is indicative of a scattering structure that can be correlated with a particular two or three particle complex.

As noted above, the present invention readily lends itself to an assay of a plurality, preferably up to four, of different analytes simultaneously. For example, one can provide a plurality of classes of finely divided particles 22, each of such classes being, of course, limited to its own unique, predeterminedly narrow range of particle diameters. In such case, the particles of each such class are precoated with a corresponding, different reactant capable of entering into a reaction with high specificity. For example, one can coat the four classes respectively with HIV-1 and HIV-2 polypeptides as described earlier herein, and HVA (hepatitis virus A) and HVB (hepatitis virus B) protein coat materials. The four coated classes are then simultaneously mixed with a sample solution to be assayed so as to incite a plurality of specific reactions each involving one of the antigenic coating. When swept with the ultrasonic bursts, the resulting record of scattering valleys or attenuations will indicate which agglutinates formed and can be readily correlated with the specific antigens involved. It is preferred to presweep sample 20 before introducing coated particles 22, so as to provide a background spectrum showing any scattering associated with the sample and not caused by agglutination. Correlation of valleys appearing on the record with particular agglutinates can easily be accomplished by precalibrating the system with predetermined class of particles against known analytes in a calibration test solution to thereby identify empirically which valleys correspond to particular agglutinates.

It will be appreciated that the present invention contemplates the formation of agglutinates by direct specific reaction between the analyte being assayed and the reagent coated on the particles. For example, where antigenic material is coated onto the particles, the latter will specifically react with antibody present in the sample fluid to form agglutinates. Conversely a similar result will occur where the antibody is coated onto the particles and allowed to specifically react directly with the antigen in the sample fluid. Alternatively, the present invention is applicable to known indirect types of assays such as sandwich assays, competition assays and the like, in which cases, the dimensions of the initial agglutinates may be different. For example, in a typical sandwich assay, the particles are coated with the same antibody for which the sample solution is to be assayed. The assay then requires the addition of a linking agent such as an antigen that will react specifically with both the free antibodies in solution and the antibodies bound to the particles, creating agglutinates that are different in dimensions than the agglutinates resulting from a direct antibody/antigen reaction.

It has also been found that the agglutination of large particles (e.g., ca. 5 μm) to one another produces less of an acoustic signal than the binding of small particles (e.g., ca. 1 μm) to the larger particle. This may occur because the simple binding of two particles of the same dimensions to one another may not change their acoustic properties to a great extent. Additionally, particle size has a distinct effect on immunological activity. For example, small particles (e.g.,<1 μm) typically have more surface area per unit volume and more rapid mass action at room temperature than larger particles. Consequently, the smaller particles appear to be better suited for agglutination reactions. However, particles that are large enough to provide scattering or attenuation to frequencies within the bandwidth (100–200 MHz) of easily obtained transducers appear to be less effective in immunological reactions.

Another embodiment of the present invention therefore employs a combination of such small, highly reactive particles with the larger, less reactive particles. Such combination provides the good immunological properties of the smaller particles with the acoustic utility of the larger particles, and thus appears to be optimum for transducers operative in the 100–200 MHz range. In this embodiment, the sensor is selected to have a bandwidth that normally will detect acoustic scattering by both the larger particles and conjugates initially formed by reaction among the particles of the two classes, but will not detect the smaller particles per se inasmuch as they are too small to exhibit acoustic scattering within the bandwidth of the sensor. Typically, one may thus employ larger particles that have average diameters at least twice as large as the smaller particles, for example, the larger particles lying in the range of about 4.5 µm to about 10 µm and the smaller particles being typically in the range of about 0.5 µm to about 1.5 gm.

Thus the latterly-described embodiment may employ several different types of immunological or specific binding reaction to effect agglutination. The following examples are described, for convenience, in terms of antigen and antibody, but it will be understood that other specific binding reactants may also be employed. In one example, autoagglutination can be effected by coating antigen on the particles of one class and antibody on the articles of the other class. In another example, by placing the same antigen on both particle sizes, agglutination will occur in the presence of the specific antibody except where free antigen is present. In yet another example, by placing antibody on both particle sizes, agglutination will occur in the presence of the specific antigen.

Since certain changes may be made in the above process and apparatus without departing from the scope of the invention herein involved, it is intended that all matter contained in the above description or shown in the accompanying drawing shall be interpreted in an illustrative and not in a limiting sense.

What is claimed is:

1. Apparatus for assaying a fluid sample for an analyte, said apparatus comprising, in combination a first reagent including at least a first class of minute initial particles dimensioned within a predeterminedly narrow range of particle diameters and being coated with a reactant capable of entering into a reaction involving said analyte so as to generate resultant particles from said initial particles and of different dimensions than said initial particles, said resultant particles having characteristic acoustic scattering cross sections;

at least a second class of minute, substantially spheroidal particles within a predeterminedly narrow range of substantially larger particle diameters than the diameters of said particles of said first class, the particles of said second class being coated with said reactant; and means for forming a mixture of the reactant coated particles of said first and second classes with said sample so as to initiate said reaction and form said resultant particles from said first and second classes of particles by said reaction with analyte present in said sample, said means for forming a mixture comprising a hollow flow cell having a chamber of capillary cross-section with inlet and outlet conduits thereto for respectively introducing and removing the mixture of reagent and sample to and from said chamber;

means for irradiating the mixture of said reagent and sample with compressional waves in a predetermined frequency range at which said resultant particles will cause a reduction in forward energy of said waves within a wavelength band determined in accordance with the scattering cross-sections of said resultant particles;

a sonic delay line disposed between said source and said mixture so as to delay the propagation of said waves irradiating said mixture;

acoustic reflector means positioned for reflecting said waves back toward said source after having traversed said mixture;

sensor means for detecting said reduction of said forward energy by said resultant particles, said sensor means comprising means for generating electrical signals in accordance with the detected reduction in said forward energy; and means for determining from the frequency and amplitude of said electrical signals an assay of said analyte in said sample.

2. Apparatus for assaying a fluid sample for an analyte, said apparatus comprising, in combination a first reagent including at least a first class of minute initial particles dimensioned within a predeterminedly narrow range of particle diameters and being coated with a reactant capable of entering into a reaction involving said analyte so as to generate resultant particles from said initial particles and of different dimensions than said initial particles, said resultant particles having characteristic acoustic scattering cross sections;

at least a second class of minute, substantially spheroidal particles within a predeterminedly narrow range of substantially larger particle diameters than the diameters of said particles of said first class, the particles of said second class being coated with said reactant; and means for forming a mixture of the reactant coated particles of said first and second classes with said sample so as to initiate said reaction and form said resultant particles from said first and second classes of particles by said reaction with analyte present in said sample; and means for irradiating the mixture of said reagent and sample with compressional waves in a predetermined frequency range at which said resultant particles will cause a reduction in forward energy of said waves within a wavelength band determined in accordance with the scattering cross-sections of said resultant particles; and sensor means for detecting said reduction of said forward energy by said resultant particles.

3. Apparatus for assaying a fluid sample as set forth in claim 2 wherein said first class of said particles is selected such that they exhibit acoustic scattering substantially outside of the bandwidth of said sensor means, and the bandwidth of said sensor means is selected so as to detect acoustic scattering by both said second class of said particles and said conjugates formed by reaction among said first and second classes of particles.

4. Apparatus for assaying a fluid sample as set forth in claim 2 wherein the average diameter within the range of said second class of said particles is at least twice the average diameter within the range of said first class of said particles.

5. Apparatus for assaying a fluid sample as set forth in claim 2 wherein said particles of said first class have diameters between 0.5±µm to about 1.5±0.1 µm, and said particles of said second class have diameters between 4.5±0.1 µm to about 10 ±0.1 µm in diameter.

6. Apparatus as set forth in claim 2 wherein
said first class of initial particles are linked conjugates of smaller, substantially spheroidal particles, said linked conjugates being cleaved by said reaction so as to release said spheroidal particles as resultant particles of different dimensions than said initial particles.

7. Apparatus for assaying a fluid sample for an analyte, said apparatus comprising, in combination a first reagent including at least a first class of minute initial particles dimensioned within a predeterminedly narrow range of particle diameters, said particles comprising a reactant capable of entering into a reaction involving said analyte so as to generate resultant particles of different dimensions than said initial particles, said resultant particles having characteristic acoustic scattering cross sections;

means for forming a mixture of said reagent with said fluid sample so as to initiate said reaction;

a source of ultrasonic waves for irradiating the mixture of said reagent and sample with said waves in a predetermined frequency range at which said resultant particles will cause a reduction in forward energy of said waves within a wavelength band determined in accordance with the scattering cross-sections of said resultant particles;

an ultrasonic delay line disposed between said source and said mixture so as to delay the propagation of said waves irradiating said mixture; and sensor means for detecting said reduction of said forward energy by said resultant particles.

8. Apparatus for assaying a fluid sample for an analyte, said apparatus comprising, in combination a first reagent including at least a first class of minute initial particles dimensioned within a predeterminedly narrow range of particle diameters, said particles comprising a reactant capable of entering into a reaction involving said analyte so as to generate resultant particles of different dimensions than said initial particles, said resultant particles having characteristic acoustic scattering cross sections;

means for forming a mixture of said reagent with said fluid sample so as to initiate said reaction;

a source of ultrasonic waves for irradiating the mixture of said reagent and sample with said waves in a predetermined frequency range at which said resultant particles will cause a reduction in forward energy of said waves within a wavelength band determined in accordance with the scattering cross-sections of said resultant particles;

acoustic reflector means positioned for reflecting said ultrasonic waves back toward said source after having traversed said mixture; and sensor means for detecting said reduction of said forward energy by said resultant particles.

9. Apparatus for assaying a fluid sample as set forth in claim 8 wherein said acoustic reflector means is aligned so that the reflected waves are reflected back toward said source in a direction substantially parallel to the incident waves from said source.

10. Apparatus for assaying a fluid sample as set forth in claim 9 wherein said acoustic reflector means is shaped substantially as a 90° hollow cone.

11. Apparatus for assaying a fluid sample for an analyte, said apparatus comprising, in combination a first reagent including at least a first class of minute initial particles dimensioned within a predeterminedly narrow range of particle diameters, said particles comprising a reactant capable of entering into a reaction involving said analyte so as to generate resultant particles of different dimensions than said initial particles, said resultant particles having characteristic acoustic scattering cross sections;

means for forming a mixture of said reagent with said fluid sample so as to initiate said reaction, said means for forming a mixture comprising a hollow flow cell having a chamber of capillary cross-section with inlet and outlet conduits thereto for respectively introducing and removing the mixture of reagent and sample to and from said chamber;

a source of ultrasonic waves for irradiating the mixture of said reagent and sample with said waves in a predetermined frequency range at which said resultant particles will cause a reduction in forward energy of said waves within a wavelength band determined in accordance with the scattering cross-sections of said resultant particles; and sensor means for detecting said reduction of said forward energy by said resultant particles.

12. Apparatus for assaying a fluid sample as set forth in claim 11 wherein said means for irradiating said resultant particles with compressional waves comprises an acoustic transducer mounted adjacent one side of said chamber so that the direction of acoustic propagation from said transducer is directed substantially normally to the direction of fluid flow through said chamber.

13. Apparatus for assaying a fluid sample as set forth in claim 11 including an air vent coupled to said chamber, the cross-section dimension of said vent being substantially less than the cross-section dimension of said outlet conduit.

14. Apparatus for assaying a fluid sample for an analyte, said apparatus comprising, in combination a first reagent including at least a first class of minute initial particles dimensioned within a predeterminedly narrow range of particle diameters, said particles comprising a reactant capable of entering into a reaction involving said analyte so as to generate resultant particles of different dimensions than said initial particles, said resultant particles having characteristic acoustic scattering cross sections;

means for forming a mixture of said reagent with said fluid sample so as to initiate said reaction, means for irradiating the mixture of said reagent and sample with compressional waves in a predetermined frequency range at which said resultant particles will cause a reduction in forward energy of said waves within a wavelength band determined in accordance with the scattering cross-sections of said resultant particles, said means for irradiating comprising acoustic transducer means for providing said compressional waves;

sensor means for detecting said reduction of said forward energy by said resultant particles, said sensor means comprising means for generating electrical signals in accordance with the detected reduction in said forward energy; and means for determining from the frequency and amplitude of said electrical signals an assay of said analyte in said sample.

15. Apparatus for assaying a fluid sample as set forth in claim 14 wherein said transducer means comprises a sonic generator for providing said compressional waves and also includes said sensor means for detecting said change in said forward energy and for producing said electrical signals.

16. Apparatus for assaying a fluid sample as set forth in claim 14 wherein said transducer means is operable to produce said compressional waves as a continuous excitation.

17. Apparatus for assaying a fluid sample as set forth in claim 16 wherein said excitation is at a single frequency.

18. Apparatus for assaying a fluid sample as set forth in claim 16 wherein said excitation is continuously varied in a sawtooth or triangular format to produce a spectrum as a function of time.

19. Apparatus for assaying a fluid sample as set forth in claim 16 wherein said excitation is a continuous signal composed of a superposition of individual signals of single frequencies, each corresponding to a wavelength of interest.

20. Apparatus for assaying a fluid sample as set forth in claim 16 wherein said transducer means is operable to produce said compressional waves as a plurality of sonic pulses having wideband spectra.

21. Apparatus for assaying a fluid sample as set forth in claim 20 wherein said transducer means includes means for introducing a delay into the propagation of said pulses through said mixture sufficient to permit said transducer means to switch between transmission and reception of the energy of the compressional waves.

22. Apparatus for assaying a fluid sample as set forth in claim 20 including:
  a flow cell defining a hollow, capillary flow channel having inlet and outlet ends, said channel being directed substantially normally to the direction of acoustic propagation from said transducer means;
  acoustic reflector means positioned so that said channel is disposed between said transducer means and said reflector means;
  a narrow, vertical, open air vent having an internal diameter much smaller than the diameter of said channel and disposed adjacent said outlet end of said channel for coupling the outside of said cell with said channel.

23. Apparatus for assaying a fluid sample as set forth in claim 22 wherein the cross-section dimension of said channel is several thousandths of an inch.

24. Apparatus for assaying a fluid sample as set forth in claim 22 wherein said acoustic reflector means is aligned to reflect said compressional waves back toward said transducer means within about 1 angular degree of the direction of propagation of said waves from said transducer means.

25. Apparatus for assaying a fluid sample as set forth in claim 22 wherein said acoustic reflector means is configured as a hollow 90° cone which provides the property of returning the compressional wave reflected therefrom in a direction substantially parallel to the compressional wave incident thereon.

26. Apparatus for assaying a fluid sample as set forth in claim 14 wherein said means for determining the frequency and amplitude of said electrical signals comprises:
  means for amplifying said electrical signals;
  voltage controlled oscillator means for producing a sinusoidal signal;
  mixer means for multiplying the amplified signals with said sinusoidal signal from said voltage controlled oscillator means so as to produce multiplied signals;
  filter means for rejecting signal components in said multiplied signals so as to produce corresponding low frequency signals;
  means for detecting said low frequency signals;
  sample-and-hold circuit means for storing said low frequency signals;
  means coupled to the output of said sample-and-hold circuit means for continuously compared the signals stored in said sample-and-hold circuit means with signal common to produce error signals;
  means for applying said error signals to said voltage-controlled oscillator means so as to control the frequency of the latter, said error signals providing a measure of the frequency of said change of said forward energy, the signals stored in said sample-and-hold circuit means representing the amplitude of said change.

27. Apparatus for assaying a fluid sample as set forth in claim 26 wherein
  said filter means is a bandpass filter;
  said means for detecting said low frequency signals is a detector; and
  said sample-and-hold circuit means is a sample-and-hold circuit.

28. Apparatus for assaying a fluid sample as set forth in claim 26 wherein
  said filter means comprises a plurality of bandpass filters;
  said means for detecting said low frequency signals comprises a plurality of detectors; and
  said sample-and-hold circuit means comprises a plurality of sample-and-hold circuits.

29. Method of assaying for at least one type of analyte in a liquid sample, including the steps of
  providing a first reagent including at least a first class of minute particles dimensioned within a predeterminedly narrow range of particle diameters and being coated with a reactant capable of entering into a reaction involving said analyte so as to generate resultant particles of different dimensions than said first class of initial particles, said resultant particles having characteristic acoustic scattering cross sections;
  providing a second reagent including at least a second class of substantially larger particle diameters than the diameters of said particles of said first class, the particles of said second class being coated with said first reactant;
  forming a mixture of the reactant coated particles of said first and second classes with said sample so as to effect a specific reaction involving said reactant and said analyte to form conjugates of said first and second classes of particles, said conjugates having a characteristic acoustic scattering cross-sections;
  irradiating the conjugates with compressional waves in a predetermined frequency range at which said conjugates will cause a reduction in forward energy of said waves within a wavelength band determined in accordance with said scattering cross-sections; and
  detecting said reduction of said forward energy.

30. In a method as defined in claim 29 including the steps of coating a plurality of particles of a plurality of said classes with a reactant unique to each such class and couplable with a different analyte in said sample, and
  mixing said reactant coated particles of each of said classes with said sample so as to effect a specific reaction involving each of said reactants and the corresponding one of said different analytes to form respective conjugates of said particles.

31. In a method as defined in claim 29 including the steps of coating a plurality of particles of each of a plurality of said classes with a plurality of types of reactant unique to that class, each of said plurality of types of reactant being couplable with a distinct analyte so as to form corresponding conjugates.

32. In a method as defined in claim 29 wherein said initial particles of said first class are selected as minute, substantially spheroidal particles coated with a reactant capable of entering into a binding reaction with high specificity with said analyte to form resultant particles that are conjugates of said initial particles; and said change in forward energy is a reduction.

33. In a method as defined in claim 29 wherein said initial particles of said first class are selected as linked conjugates of smaller particles reactable with said analyte to cleave the linkages in said conjugates so as to form resultant particles that are said smaller particles.

34. In a method as defined in claim 29 including the steps of providing a plurality of up to four of said classes of finely divided, substantially spheroidal particles, each of said classes being limited to a unique, predeterminedly narrow range of particle diameters;

coating the particles of each of said classes coated with a corresponding, different reactant capable of entering into a reaction with high specificity; and forming a simultaneous mixture of said reagent coated particles with said sample so as to incite a plurality of specific reactions each involving one of said reagents and a corresponding type of analyte to form conjugates of said particles.

35. In a method as defined in claim 29, including the steps of introducing said compressional waves in said frequency range into a fluid free of said resultant particles so as to determine the forward energy of said waves propagated through said fluid; and comparing the forward energy of said waves propagated through said fluid with said change in forward energy in said waves propagated through said mixture of reagent and fluid sample.

36. In a method as defined in claim 29 wherein said liquid sample is whole blood.

* * * * *